US012779095B2

(12) United States Patent
Hasebe et al.

(10) Patent No.: US 12,779,095 B2
(45) Date of Patent: Nov. 3, 2026

(54) METAL MATERIAL FOR MEDICAL DEVICE, METHOD OF MANUFACTURING METAL MATERIAL FOR MEDICAL DEVICE, AND MEDICAL DEVICE

(71) Applicants: Terumitsu Hasebe, Kawasaki (JP); Global Vascular Co., Ltd., Tokyo (JP)

(72) Inventors: Terumitsu Hasebe, Kawasaki (JP); Shunto Maegawa, Toyama (JP)

(73) Assignees: Terumitsu Hasebe, Kanagawa (JP); Global Vascular Co., Ltd., Tokyo (JP)

( * ) Notice: Subject to any disclaimer, the term of this patent is extended or adjusted under 35 U.S.C. 154(b) by 653 days.

(21) Appl. No.: 18/035,545

(22) PCT Filed: Nov. 9, 2020

(86) PCT No.: PCT/JP2020/041737
§ 371 (c)(1),
(2) Date: May 5, 2023

(87) PCT Pub. No.: WO2022/097300
PCT Pub. Date: May 12, 2022

(65) Prior Publication Data

US 2024/0009358 A1 Jan. 11, 2024

(51) Int. Cl.
*A61L 31/08* (2006.01)
*A61F 2/82* (2013.01)
(Continued)

(52) U.S. Cl.
CPC .............. *A61L 31/084* (2013.01); *A61F 2/82* (2013.01); *A61L 31/022* (2013.01); (Continued)

(58) Field of Classification Search
CPC .... A61L 31/022; A61L 31/024; A61L 31/084; A61L 31/088; A61L 31/10; A61L 31/128; A61L 2420/08; A61L 29/02; A61L 29/08; A61L 29/103; A61L 29/12; A61F 2/0077; A61F 2/82; A61F 2310/0058; A61F 2210/0076; C23C 14/0605; C23C 16/26;
(Continued)

(56) References Cited

U.S. PATENT DOCUMENTS 7,931,934 B2 4/2011 Nakatani et al.
2009/0209942 A1* 8/2009 Nakatani ............... A61L 31/088 604/528
2012/0177936 A1* 7/2012 Suzuki ...................... A61F 2/88 606/1

FOREIGN PATENT DOCUMENTS

JP 2001-029447 A 2/2001
JP 2012-041629 A 3/2012
(Continued)

OTHER PUBLICATIONS

Tatsuyuki Nakatani, "Application of Bio-compatible DLC Coatings to Medical Devices", Journal of The Surface Finishing Society of Japan, 2016, vol. 67, No. 6, p. 279-283.
(Continued)

*Primary Examiner* — Robert A Lynch
(74) *Attorney, Agent, or Firm* — Banner & Witcoff, Ltd.

(57) ABSTRACT

The present disclosure provides a metal material for a medical device, the metal material including a metal layer, and a diamond-like carbon layer provided on the metal layer and containing fluorine and silicon.

17 Claims, 6 Drawing Sheets

(51) Int. Cl.

| | |
|---|---|
| ***A61L 31/02*** | (2006.01) |
| ***A61L 31/12*** | (2006.01) |
| ***C23C 14/06*** | (2006.01) |
| ***C23C 16/26*** | (2006.01) |

(52) U.S. Cl.
CPC ..... *A61L 31/128* (2013.01); *A61F 2210/0076* (2013.01); *A61L 2420/08* (2013.01); *C23C 14/0605* (2013.01); *C23C 16/26* (2013.01)

(58) Field of Classification Search
CPC ..... C23C 16/30; C23C 28/044; C23C 28/046; C23C 28/048; C23C 28/343; C23C 28/36
See application file for complete search history.

(56) References Cited

FOREIGN PATENT DOCUMENTS

| | | | |
|---|---|---|---|
| JP | 5536168 | B2 | 7/2014 |
| JP | 5661632 | B2 | 1/2015 |
| KR | 10-2009-0017584 | A | 2/2009 |

OTHER PUBLICATIONS

Dec. 8, 2020 (WO) Translation of the Written Opinion of the International Searching Authority.

* cited by examiner

METAL MATERIAL FOR MEDICAL DEVICE, METHOD OF MANUFACTURING METAL MATERIAL FOR MEDICAL DEVICE, AND MEDICAL DEVICE

RELATED APPLICATIONS

This application is a National Stage Application under 35 U.S.C. 371 of co-pending PCT application PCT/JP2020/041737 designating the United States and filed Nov. 9, 2020, which is hereby incorporated by reference in its entirety.

TECHNICAL FIELD

The present disclosure relates to a metal material for a medical device, a method of manufacturing a metal material for a medical device, and a medical device.

TECHNICAL FIELD

A film of diamond-like carbon (DLC) is known as an amorphous carbon film, and has a hard, dense, and inactive surface, and thus is applied in various fields.

For example, a technique of imparting characteristics such as abrasion resistance, corrosion resistance, and surface smoothness to a surface of a substrate using an inorganic material such as metal or ceramic or an organic material such as resin, by forming a DLC film on the surface of the substrate, has been studied. Specifically, there is known a metal mold or a metal tool in which durability is enhanced by coating a metal surface with DLC to cover the metal surface with a DLC film. Furthermore, the DLC film is also used for medical instruments (stents and the like). For example, it has been studied to enhance durability by providing the DLC film on a surface of a metal used for the medical instruments.

As a specific example, Japanese Patent (JP-B2) No. 5536168 discloses a super-hydrophilic material including a DLC film having a hydrophilic functional group on a surface of a substrate, in which an intermediate layer for improving adhesion between the substrate and the DLC film is provided between the substrate and the DLC film.

Furthermore, Japanese Patent (JP-B2) No. 5661632 discloses a stent including a substrate layer having a surface made of a metal material, a carbon compound layer made of silicon carbide, a first diamond-like carbon layer containing at least silicon and not containing fluorine, and a second diamond-like carbon layer (F-DLC layer) containing fluorine, in which an atom percent concentration of the silicon constituting the first diamond-like carbon layer is 1% or more and 10% or less.

SUMMARY OF INVENTION

Technical Problem

As described above, a technique using a film of diamond-like carbon (DLC film) has been studied also in devices for medical use (hereinafter, medical devices) such as stents. Among the conventional techniques, the stent described in JP-B2 No. 5661632 is considered to suppress the occurrence of cracking and peeling by providing the first DLC layer containing no fluorine between the carbon compound layer and the F-DLC layer. As a conventional medical device using a DLC film, a device (the metal material 30 for a medical device) having a layered structure of an F-DLC layer 32, a Si-DLC layer 36, a SiC layer 38, and a substrate 34 as shown in FIG. 13 is known.

Medical devices are typically used for a long period of time after being implanted in a living body.

Therefore, in a living body, it is required to have stable performance that the medical devices can continuously and stably follow the movement of the living body for a long period of time, and the medical devices are flexibly deformed against various stresses different in strength or direction when following the movement. However, the conventional technique has not actually achieved flexibility capable of relaxing various stresses as well as followability capable of following every movement of a living body.

The present disclosure has been made in view of the above.

A problem to be solved by an embodiment of the present disclosure is to provide a metal material for a medical device having followability of stably following movement of a living body and flexibility of flexibly deforming against various stresses at the time of following, and a method of manufacturing the same.

A problem to be solved by another embodiment of the present disclosure is to provide a medical device having followability of stably following movement of a living body and flexibility of flexibly deforming against various stresses at the time of following.

Solution to Problem

Specific means for solving the problems include the following aspects.

<1> A metal material for a medical device, the metal material including: a metal layer; and a diamond-like carbon layer provided on the metal layer and containing fluorine and silicon.

<2> The metal material for a medical device according to <1>, in which a total concentration of the fluorine contained in the diamond-like carbon layer is from 7 atom % to 10 atom % with respect to a total concentration of carbon, fluorine, and silicon.

<3> The metal material for a medical device according to <1> or <2>, in which a total concentration of the silicon contained in the diamond-like carbon layer is from 17 atom % to 25 atom % with respect to a total concentration of carbon, fluorine, and silicon.

<4> The metal material for a medical device according to any one of <1> to <3>, in which, in the diamond-like carbon layer, a concentration of the fluorine at a surface at an opposite side from a side facing the metal layer is larger than a concentration of the fluorine at a surface at the side facing the metal layer, in a thickness direction of the diamond-like carbon layer.

<5> The metal material for a medical device according to <4>, in which, in the diamond-like carbon layer, a ratio Cf of the concentration of the fluorine at the surface at the opposite side from the side facing the metal layer with respect to the concentration of the fluorine at the surface at the side facing the metal layer satisfies a relationship $1<Cf\leq 155$.

<6> The metal material for a medical device according to <4> or <5>, in which a concentration of the fluorine contained in the diamond-like carbon layer gradually increases from the side facing the metal layer toward the opposite side from the side facing the metal layer in the thickness direction of the diamond-like carbon layer.

<7> The metal material for a medical device according to any one of <1> to <6>, in which, in the diamond-like carbon layer, a concentration of the silicon at a surface at an opposite side from a side facing the metal layer is smaller than a concentration of the silicon at a surface at the side facing the metal layer, in a thickness direction of the diamond-like carbon layer.

<8> The metal material for a medical device according to <7>, in which, in the diamond-like carbon layer, a ratio Cs of the concentration of the silicon at the surface at the opposite side from the side facing the metal layer with respect to the concentration of the silicon at the surface at the side facing the metal layer satisfies a relationship $0.015 \leq Cs < 1$.

<9> The metal material for a medical device according to <7> or <8>, in which the concentration of the silicon contained in the diamond-like carbon layer gradually decreases from the side facing the metal layer toward the opposite side from the side facing the metal layer in the thickness direction of the diamond-like carbon layer.

<10> The metal material for a medical device according to any one of <1> to <9>, in which a ratio ($D^F$:$D^S$) of a concentration $D^F$ of the fluorine with respect to a concentration $D^S$ of the silicon at a surface of the diamond-like carbon layer at an opposite side from a side facing the metal layer is from 1:1 to 90:1.

<11> The metal material for a medical device according to any one of <1> to <10>, in which the diamond-like carbon layer is provided as an outermost layer on the metal layer.

<12> The metal material for a medical device according to any one of <1> to <11>, in which the metal layer contains at least one metal selected from the group consisting of titanium, nickel, cobalt, chromium, tantalum, platinum, gold, alloys thereof, and stainless steel.

<13> The metal material for a medical device according to <12>, in which the metal layer contains a nickel-titanium alloy, a cobalt-chromium alloy, or stainless steel.

<14> The metal material for a medical device according to any one of <1> to <13>, in which the metal material is used in a stent.

<15> The metal material for a medical device according to <14>, in which the stent is a stent for a systemic blood vessel.

<16> A medical device, including the metal material for a medical device according to any one of <1> to <15>.

<17> The medical device according to <16>, in which the medical device is a stent.

<18> The medical device according to <17>, in which the stent is a stent for a lower limb blood vessel.

<19> A method of manufacturing a metal material for a medical device, the method including forming a diamond-like carbon layer containing fluorine and silicon on a metal layer by vapor deposition, by a vapor phase growth method using a mixed raw material obtained by mixing a silane compound and a fluorine-containing aliphatic hydrocarbon as raw materials.

Advantageous Effects of Invention

According to an embodiment of the present invention, there are provided a metal material for a medical device having followability of stably following movement of a living body and flexibility of flexibly deforming against various stresses at the time of following, and a method of manufacturing the same. The metal material for a medical device of the present disclosure is expected to be compatible with continuous use for a long period of time.

According to another embodiment of the present invention, there is provided a medical device having followability of stably following movement of a living body and flexibility of flexibly deforming against various stresses at the time of following. The medical device of the present disclosure is expected to be compatible with continuous use for a long period of time.

DESCRIPTION OF EMBODIMENTS

Figure 1:
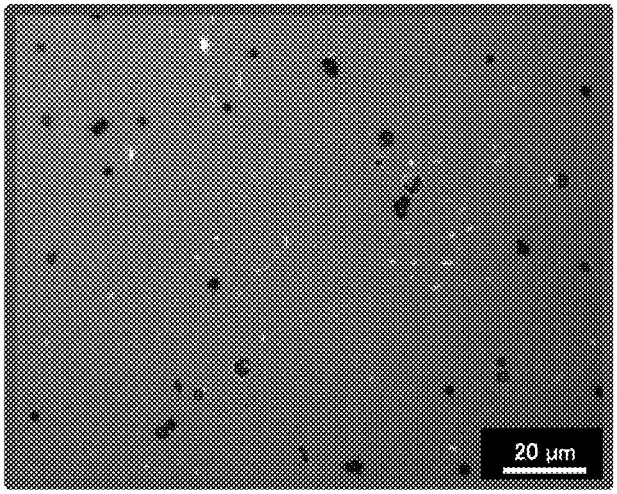
FIG. 1 is an SEM photograph illustrating an adherence state of platelets in a test sample of Example 3 in which a single layer-DLC layer is formed on a NiTi alloy substrate.

Hereinafter, the metal material for a medical device, the method of manufacturing the same, and the medical device of the present disclosure will be described in detail. The description of the components described below may be made based on a representative embodiment of the present disclosure, but the present disclosure is not limited to such an embodiment.

In the present disclosure, "(from) X to Y" indicating a numerical range is used to mean including numerical values X and Y described before and after the numerical range as a lower limit value and an upper limit value, respectively.

In the numerical range described stepwise in the present disclosure, an upper limit value or a lower limit value described in one numerical range may be replaced with an upper limit value or a lower limit value of another numerical range described stepwise. Furthermore, in the numerical range described in the present disclosure, an upper limit value or a lower limit value of the numerical range may be replaced with a value indicated in Examples.

In the present disclosure, the term "step" encompasses not only an independent step but also a step that cannot be clearly distinguished from other steps as long as the intended purpose of the step is achieved.

In the present disclosure, in a case where multiple substances corresponding to each component are present in a layer, an amount of each component of a composition means a total amount of the multiple substances present in the composition unless otherwise specified.

In the present disclosure, a combination of preferred embodiments is a more preferred embodiment.

<Metal Material for Medical Device>

The metal material for a medical device of the present disclosure includes a metal layer and a diamond-like carbon layer (hereinafter, also simply referred to as "DLC layer") provided on the metal layer and containing fluorine and silicon. The metal material for a medical device of the present disclosure may further include another layer such as an intermediate layer as necessary.

In the metal material for a medical device of the present disclosure, since the DLC layer provided on the metal layer is a layer of diamond-like carbon containing fluorine (F) and silicon (Si), the metal material has excellent stability of stably following movement of a living body, and has flexibility capable of flexibly deforming against various stresses generated according to the movement of the living body when following the movement of the living body. This provides excellent stability in the living body.

The reason why the effects of the present disclosure are exerted is not necessarily clear, but is estimated as follows.

As the DLC layer in the metal material for a medical device of the present disclosure, diamond-like carbon containing fluorine (F) and silicon (Si) is used. Generally, diamond-like carbon is considered to be hard and excellent in surface properties, but in a living body, diamond-like carbon is likely to be an attack target by platelets or the like as a foreign substance. Furthermore, movement of the living body varies, and torsional stress is often applied in addition to bending stress and tensile stress. In order to continuously and stably use in a living body for a long period of time even under such circumstances, it is required to have flexibility capable of stably following the movement of the living body and flexibly deforming against various stresses received when following the movement.

Conventionally, it has been known to use F in order to impart biocompatibility to the DLC layer at an outermost side, and it has been known to use Si in order to enhance adhesion of the DLC layer to a substrate.

In order to cope with the stress caused by the movement of the living body, it is important to have flexibility of easily following the stress and relaxing the stress. By simply providing a layer containing F or Si, interlayer adhesion tends to be insufficient, and even if properties depending on the composition can be partially exhibited, it is estimated that the balance between followability to the movement of the living body and stress relaxation (flexibility) at the time of following is not appropriate as a whole material. Therefore, the effect of suppressing cracking or peeling when receiving various stresses is small.

In the present disclosure, by using diamond-like carbon containing F and Si, it is possible to impart, to the DLC layer, followability of stably following the movement of the living body and flexibility of flexibly deforming against various stresses when following the movement.

As a result, the metal material for a medical device of the present disclosure can withstand long-term continuous use.

—Metal Layer—

The metal material for a medical device of the present disclosure includes a metal layer.

The metal layer may be of an aspect as a substrate constituting the metal material for a medical device (that is, an aspect in which the substrate is metal). Furthermore, the metal layer may be of an aspect in which the metal layer is included as a part of a substrate constituting the metal material for a medical device (for example, an aspect in which a material (resin, silicone rubber, or the like) other than a desired metal is used for the substrate).

Examples of the metal in the metal layer include iron, copper, titanium, nickel, cobalt, chromium, aluminum, zinc, manganese, tantalum, tungsten, platinum, and gold. Among the metals, it is preferable to contain at least one selected from the group consisting of titanium, nickel, cobalt, chromium, tantalum, platinum, and gold.

The metal may be an alloy of the aforementioned metals.

Examples of the metal alloy include a nickel-titanium alloy, a cobalt-chromium alloy, a copper-aluminum-manganese alloy, a copper-zinc alloy, a nickel-aluminum alloy, and stainless steel. Among the alloys, a nickel-titanium alloy, a cobalt-chromium alloy, or stainless steel is preferable.

As the stainless steel, for example, SUS316L is preferable from the viewpoint of corrosion resistance.

Among them, it is more preferable to contain at least one metal selected from the group consisting of titanium, nickel, cobalt, chromium, tantalum, platinum, gold, alloys thereof, and stainless steel, and it is still more preferable to contain at least one metal selected from the group consisting of titanium, nickel, cobalt, chromium, alloys thereof, and stainless steel.

Among them, a layer containing a nickel-titanium alloy, a cobalt-chromium alloy, or stainless steel, or a layer consisting of a nickel-titanium alloy, a cobalt-chromium alloy, or stainless steel is particularly preferable.

Note that, in a case where the metal layer is a layer consisting of a nickel-titanium alloy, a cobalt-chromium alloy, or stainless steel, the metal layer may contain metals other than nickel, titanium, cobalt, chromium, and stainless steel as long as the effects in the metal material for a medical device and the medical device of the present disclosure are not significantly impaired.

A thickness of the metal layer is not particularly limited, and may be appropriately selected according to a site in the living body applied as the medical device, a service life, or the like. In a case where the metal layer has a flat plate shape, the thickness of the metal layer may be selected according to the application, the shape, or the like. For example, in the case of a stent, the thickness of the metal layer may be, for example, in a range of from 50 μm to 250 μm. For example, in the case of a fixing plate, the thickness of the metal layer may be, for example, in a range of from 100 μm to 2000 μm. Furthermore, in a case where the metal layer has a shape such as a square shape, a circular shape, a semicircular shape, a block shape, a lump shape, or an irregular shape (for example, a fixing device such as a bolt or a screw, an artificial heart, or an artificial hip joint), the thickness may be selected according to a necessary shape or the like.

The metal layer may be produced by any method, and commercially available products on the market can also be used therefor.

—Diamond-like Carbon Layer—

The metal material for a medical device of the present disclosure includes a DLC layer on a substrate.

The DLC layer in the present disclosure is a diamond-like carbon layer containing fluorine (F) and silicon (Si). Since diamond-like carbon containing F and Si is used, followability of stably following movement of a living body and flexibility of flexibly deforming against various stresses when following can be exhibited.

The DLC layer may be a layer formed by any method as long as F and Si are contained by the method. The DLC layer can be formed using a known method such as a vapor deposition method or a sputtering method. The DLC layer in the present disclosure is preferably formed by a vapor phase growth method.

The method of forming the DLC layer by a vapor phase growth method will be described in detail in the section of a method of manufacturing a metal material for a medical device described later.

—F Concentration—

The total concentration of fluorine contained in the DLC layer is preferably from 7 atom % to 10 atom %, and more preferably from 7 atom % to 8.5 atom %, with respect to the total concentration of carbon, fluorine, and silicon.

The concentration of fluorine contained in the DLC layer can be measured by an X-ray photoelectron spectroscopy (XPS) analysis method. Specifically, the concentration of fluorine is determined by, using an XPS device, measuring the content of elements such as carbon (C), F, Si and, if necessary, oxygen (O) that are present at a surface of the F- and Si-containing DLC layer.

In the DLC layer, a concentration of fluorine (hereinafter, the concentration of fluorine may be abbreviated as "F concentration") at a surface at an opposite side from a side facing the metal layer is preferably larger than an F concentration at a surface at the side facing the metal layer, in a thickness direction of the DLC layer. In particular, in a case where the DLC layer is an outermost layer on the metal layer, it is preferable that the F concentration at the surface (that is, at the outermost surface) at the opposite side from the side facing the metal layer is larger than the F concentration at the surface at the side facing the metal layer, and it is more preferable that the F concentration at the outermost surface of the DLC layer is the largest in the thickness direction of the DLC layer.

In the DLC layer, a ratio Cf ($=C^{F1}/C^{F0}$) of the F concentration ($C^{F1}$) at the surface (preferably, at an outermost surface in a case where the DLC layer is the outermost layer) at the opposite side from the side facing the metal layer with respect to the F concentration ($C^{F0}$) at the surface at the side facing the metal layer preferably satisfies a relationship $1<Cf\leq 155$. That is, it is preferable that the F concentration increases from an inner side close to the metal layer of the DLC layer toward an outside in a layering direction of the metal layer and the DLC layer of the metal material for a medical device. This makes the metal material for a medical device excellent in flexibility and biocompatibility.

The ratio Cf more preferably satisfies a relationship of Formula 1, and still more preferably satisfies a relationship of Formula 2.

$$30<Cf\leq 85 \quad \text{Formula 1}$$

$$40<Cf\leq 75 \quad \text{Formula 2}$$

The DLC layer may be of an aspect in which the concentration of F contained in the DLC layer increases stepwise from the side facing the metal layer toward the opposite side from the side facing the metal layer in the thickness direction of the DLC layer. Preferably, it is an aspect in which the concentration of F contained in the DLC layer gradually increases from the side facing the metal layer toward the opposite side from the side facing the metal layer. The stepwise increase means that the F concentration increases with a constant or arbitrary concentration difference. In the latter aspect, it is preferable that the F concentration gradually increases in a direction away from the metal layer (direction toward the outside) from the inside close to the metal layer of the DLC layer, in the layering direction of the metal layer and the DLC layer of the metal material for a medical device. As a result, the metal material for a medical device has flexibility capable of flexibly deforming against various stresses caused by movement of a living body while maintaining biocompatibility of the metal material for a medical device, and has an excellent effect of suppressing cracking and peeling.

—Si Concentration—

The total concentration of silicon contained in the DLC layer is preferably from 17 atom % to 25 atom %, and more preferably from 20 atom % to 25 atom %, with respect to the total concentration of carbon, fluorine, and silicon.

The concentration of silicon contained in the DLC layer can be measured by an X-ray photoelectron spectroscopy (XPS) analysis method, similarly to the F concentration described above.

In the DLC layer, a concentration of silicon (hereinafter, the concentration of silicon may be abbreviated as "Si concentration") at the surface at the opposite side from the side facing the metal layer is preferably smaller than a Si concentration at the surface at the side facing the metal layer in the thickness direction of the DLC layer. In particular, in a case where the DLC layer is an outermost layer on the metal layer, the Si concentration at the surface at the side facing the metal layer is preferably larger than the Si concentration at the surface (that is, at the outermost surface) at the opposite side from the side facing the metal layer.

In the DLC layer, a ratio Cs ($=C^{S1}/C^{S0}$) of the Si concentration ($C^{S1}$) at the surface at the opposite side from the side facing the metal layer with respect to the Si concentration ($C^{S0}$) at the surface at the side facing the metal layer preferably satisfies a relationship $0.015\leq Cs<1$. That is, it is preferable that the Si concentration increases toward the inner side close to the metal layer of the DLC layer in the layering direction of the metal layer and the DLC layer of the metal material for a medical device. This makes the metal material excellent in deformability of deforming following the movement of the living body.

The deformability refers to a property capable of changing a shape in accordance with bending, pulling, twisting, or the like that the metal material for a medical device receives due to the movement of the living body.

The ratio Cs more preferably satisfies a relationship of Formula 3, and still more preferably satisfies a relationship of Formula 4.

$$0.3\leq Cs<1 \quad \text{Formula 3}$$

$$0.3\leq Cs<0.8 \quad \text{Formula 4}$$

The DLC layer may be of an aspect in which the concentration of Si contained in the DLC layer decreases stepwise from the side facing the metal layer toward the opposite side from the side facing the metal layer in the thickness direction of the DLC layer. Preferably, it is an aspect in which the concentration of Si contained in the DLC layer gradually decreases from the side facing the metal layer toward the opposite side from the side facing the metal layer. The stepwise decrease means that the F concentration decreases with a constant or arbitrary concentration difference. In the latter aspect, it is preferable that the Si concentration gradually increases toward the inner side close to the metal layer of the DLC layer in the layering direction of the metal layer and the DLC layer of the metal material for a medical device. As a result, deformability in which the metal material for a medical device deforms following a force such as bending, pulling, or twisting that the metal material for a medical device receives due to the movement of the living body is obtained, and the effect of suppressing cracking and peeling is excellent.

A ratio ($D^F$:$D^S$) of the F concentration $D^F$ with respect to the Si concentration $D^S$ at the surface of the DLC layer at the opposite side from the side facing the metal layer is preferably from 1:1 to 90:1, more preferably from 1:1 to 80:1, and still more preferably from 1:1 to 50:1.

When the ratio ($D_F$:$D^S$) at the surface at the opposite side from the side facing the metal layer is within the aforementioned range, a composition is obtained in which F is contained more than Si at a certain range at the surface of the DLC layer farthest from the metal layer. This makes it possible to more flexibly deform against various stresses while following the movement of the living body. This is more remarkable in a case where the DLC layer is the outermost layer of the metal material for a medical device.

As described above, the DLC layer is preferably provided as the outermost layer on the metal layer in terms of being capable of more flexibly deforming against various stresses while following the movement of the living body.

The thickness of the DLC in the present disclosure is preferably thin from the viewpoint of applications of medical devices. For example, the thickness is preferably in a range of 10 nm or more and less than 1000 nm, more preferably in a range of from 100 nm to 500 nm, and still more preferably in a range of from 150 nm to 250 nm.

The metal material for a medical device of the present disclosure may be of any aspect as long as the metal material includes a DLC layer containing F and Si on the metal layer. As a specific aspect of the metal material for a medical device, an aspect having the following layered structure may be used.

(1) DLC layer containing F and Si/metal layer (2) DLC layer containing F and Si/DLC layer not containing F and Si/metal layer (3) DLC layer containing F and Si/DLC layer containing Si/metal layer (4) DLC layer containing F and Si/intermediate layer other than DLC layer/metal layer Among the above, from the viewpoint of flexibility and stability in a living body, an aspect in which the DLC layer and the metal layer are in contact with each other and the DLC layer is the outermost layer of the metal material for a medical device is preferable, and the aforementioned aspect (1) is particularly preferable.

Figure 11:
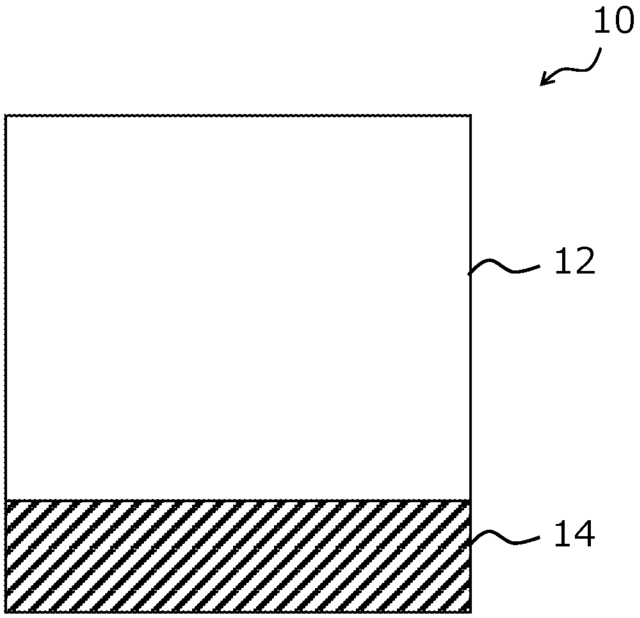
FIG. 11 is a schematic cross-sectional view illustrating an example of the metal material for a medical device of the present disclosure.

An example of the metal material for a medical device of the present disclosure is shown in FIG. 11.

The metal material 10 for a medical device shown in FIG. 11 is an example of the above (1), and a DLC layer 12 containing F and Si is layered on a metal layer 14. In the case of the aspect (2), a layered structure is obtained in which a DLC layer not containing F and Si is provided between the DLC layer 12 and the metal layer 14 in FIG. 11.

Figure 12:
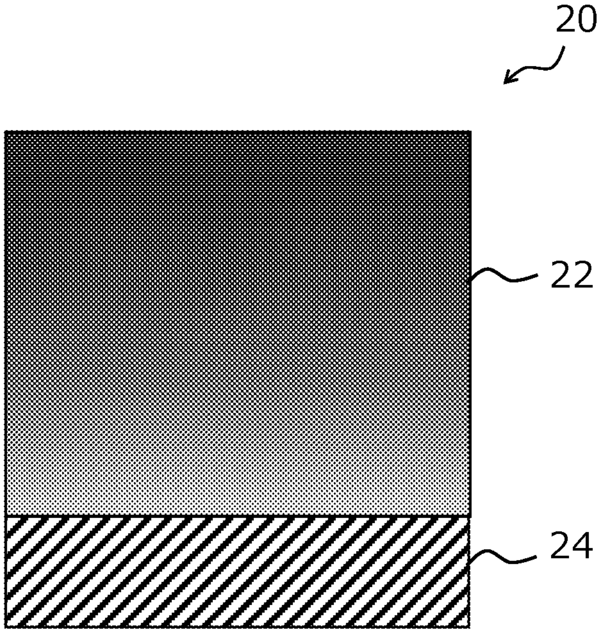
FIG. 12 is a schematic cross-sectional view illustrating another example of the metal material for a medical device of the present disclosure.

Another example of the metal material for a medical device of the present disclosure is shown in FIG. 12.

The metal material 20 for a medical device shown in FIG. 12 is another example of the above (1), and a DLC layer 22 containing F and Si and having an F concentration gradually increasing from a side (that is, from a side close to a metal layer) facing a metal layer 24 toward an opposite side (that is, toward a side away from the metal layer) from the side facing the metal layer in a thickness direction of the DLC layer is layered on the metal layer 24. That is, in the thickness direction of the DLC layer, the F concentration at the surface at the opposite side from the side close to the metal layer is larger than the F concentration at the surface at the side close to the metal layer 24. In this aspect, the Si concentration gradually decreases from the side facing the metal layer 24 toward the opposite side from the side facing the metal layer 24 in the thickness direction of the DLC layer.

Note that, in the layered structure described above, the "DLC layer not containing F and Si" refers to a DLC layer that may contain other atoms as long as F and Si are not contained. "Not containing F and Si" means that the contents of F and Si with respect to the total number of atoms of carbon, fluorine and silicon in the DLC layer are each less than 1.0 atom %.

The "DLC layer containing Si" refers to a DLC layer that contains Si and may contain atoms other than F and Si as long as F is not contained. "Not containing F" means that the content of F with respect to the total number of atoms of carbon, fluorine, and silicon in the DLC layer is less than 1.0 atom %.

Examples of the "intermediate layer other than the DLC layer" include a layer including silicon carbide (SiC), titanium carbide (TiC), chromium carbide ($Cr_3C_2$), titanium silicon carbide ($Ti_3SiC_2$), or the like.

The application of the metal material for a medical device of the present disclosure is not particularly limited.

Examples of the application of the metal material for a medical device include stents, catheter devices, endoscope devices, and fixing devices such as bolts and screws.

The stent is suitable as a stent for a blood vessel. The stent refers to a medical device that expands a tubular portion (for example, a blood vessel) of a human body from the inside of a lumen. A stent as the metal material for a medical device of the present disclosure is used for a systemic blood vessel of a human body (stent for a systemic blood vessel), and is suitable for application in a blood vessel such as a cerebral blood vessel, a pulmonary blood vessel, a cardiovascular blood vessel (for example, a coronary artery), a trunk blood vessel (for example, a superior mesenteric artery, a common hepatic artery), and a lower limb blood vessel (for example, a lower limb vein).

Among them, the metal material for a medical device of the present disclosure is preferably applied to a blood vessel having a large movement such as bending, pulling, and twisting from the viewpoint of more effectively exhibiting the effect, and is preferably used, for example, as a stent for a cardiovascular blood vessel or a lower limb blood vessel.

<Method of Manufacturing Metal Material for Medical Device>

The method of manufacturing the metal material for a medical device of the present disclosure includes a step (hereinafter, DLC layer forming step) of forming a diamond-like carbon layer (DLC layer) containing fluorine and silicon on a metal layer, by a vapor phase growth method using a mixed raw material obtained by mixing a silane compound and a fluorine-containing aliphatic hydrocarbon as raw materials. The method of manufacturing the metal material for a medical device of the present disclosure may further include other steps as necessary.

—DLC Layer Forming Step—

In the DLC layer forming step in the present disclosure, the diamond-like carbon layer containing fluorine and silicon is formed on the metal layer by vapor deposition, by the vapor phase growth method using the mixed raw material obtained by mixing a silane compound and a fluorine-containing aliphatic hydrocarbon.

The vapor phase growth method encompasses a chemical vapor deposition method (CVD method), a physical vapor deposition method (PVD method), and the like.

Examples of the CVD method include a plasma enhanced chemical vapor deposition method (PE-CVD method) and a thermal chemical vapor deposition method. A thin film containing F, Si, and C can be formed by thin film synthesis using the PE-CVD method.

The PE-CVD method is a type of chemical vapor deposition (CVD) method using a gas as a raw material, and is a method in which a raw material gas is introduced into a vacuum vessel, and plasma is generated to cause a chemical reaction, thereby depositing a film. The CVD method is a generic term for a method of depositing a film on a substrate using a chemical reaction.

As an energy source for causing the chemical reaction, heat, plasma, laser, or the like is used. In the CVD method, a gas is used as a raw material. Therefore, the quality of the film that can be formed can be freely changed by selecting the raw material gas, and various elements can be added as desired.

In the present disclosure, the DLC layer can be suitably formed by the CVD method. As a result, film formation conditions (for example, various parameters) can be controlled as desired, and are suitable for formation of the DLC layer in which the F concentration and the Si concentration change in the thickness direction of the DLC layer.

In the PE-CVD method, a hydrocarbon gas or a gas containing an element to be added is caused to flow as a raw material gas into a vacuum vessel, and plasma is generated to cause a chemical reaction, thereby depositing a film. As the power for generating plasma, DC power and AC power such as high frequency and microwave are suitably used. In the PE-CVD method, a chemical species having a high degree of activation can be reacted by using plasma, and the reaction can be performed at a low temperature.

The DLC layer in the present disclosure can be formed using an inductively coupled high frequency plasma chemical vapor deposition (ICP-CVD) device using a high frequency. As an ICP-CVD device, for example, YH-100NX manufactured by ONWARD GIKEN Co., Ltd. can be used.

In the ICP-CVD device, plasma is generated between ring-shaped electrodes by high-frequency discharge, and a bias voltage is applied to a jig on which a substrate is placed, so that ionized or excited chemical species are adsorbed to deposit and form a film. As film formation conditions, parameters such as a processing time, a high-frequency output, a bias voltage, a raw material gas flow rate, a high-frequency pulse amplitude, a bias pulse amplitude, and a high-frequency voltage, a bias voltage, and a raw material gas flow rate at the time of plasma ignition can be controlled.

Examples of the PVD method include a plasma ion implantation method, a vacuum vapor deposition method, and a sputtering method.

As the raw material, a mixed raw material obtained by mixing a silane compound and a fluorine-containing aliphatic hydrocarbon is used.

As the silane compound, an organosilicon compound containing carbon is preferable. Examples of the organosilicon compound include a compound represented by the following Formula S.

$$SiR_xH_{4-x}: \qquad \text{Formula S}$$

In Formula S, each of R represents an alkyl group having 1 to 4 carbon atoms, and x represents an integer of 1 to 4.

Examples of the compound represented by Formula S include tetramethylsilane, tetraethylsilane, trimethylsilane, diethylsilane, methyldiethylsilane, and diethyldimethylsilane.

As the fluorine-containing aliphatic hydrocarbon, a fluorine-containing aliphatic hydrocarbon having 1 to 4 carbon atoms is preferable, and a perfluoro hydrocarbon having 1 to 4 carbon atoms is more preferable. Examples of the fluorine-containing aliphatic hydrocarbon include tetrafluoromethane ($CF_4$), hexafluoroethane ($C_2F_6$), octafluoropropane, and perfluorobutane ($C_4F_{10}$).

As the raw material, a hydrocarbon can be further used.

In the case of the CVD method, a saturated hydrocarbon (for example, methane ($CH_4$), ethane ($C_2H_6$), and the like), an unsaturated hydrocarbon (for example, acetylene ($C_2H_2$), benzene ($C_6H_6$), and the like), or the like can be used as the hydrocarbon.

In the case of the PVD method, solid carbon can be used as the hydrocarbon.

In the DLC layer forming step, the silane compound is vaporized, and the vaporized silane compound and the fluorine-containing aliphatic hydrocarbon (unsaturated hydrocarbons may be added) are introduced into a chamber to form a film. At this time, it is preferable to control and gradually change the partial pressures of the silane compound and the fluorine-containing aliphatic hydrocarbon. The mixed raw material of the silane compound and the fluorine-containing aliphatic hydrocarbon can form the DLC layer in the present disclosure by controlling and mixing the silane compound and the fluorine-containing aliphatic hydrocarbon at an arbitrary ratio. For example, it can be performed as follows.

That is, a silane compound and a fluorine-containing aliphatic hydrocarbon are first supplied to a surface of the metal layer at a mixing ratio of the silane compound≥a mixing ratio of the fluorine-containing aliphatic hydrocarbon, and adsorbed and deposited. At the start of film formation, only a silane compound may be used without using a mixed material. Subsequently, the film is continuously formed by adsorption and deposition while decreasing (preferably gradually decreasing) the mixing ratio of the silane compound and increasing (preferably gradually increasing) the mixing ratio of the fluorine-containing aliphatic hydrocarbon.

By forming the film in this manner, a DLC layer is obtained which has a composition distribution in which the amount of F increases (preferably, the amount of F gradually increases) and the amount of Si decreases (preferably, the amount of Si gradually decreases) in a deposition direction (thickness direction of the layer to be deposited) from the side of the metal layer.

—Other Steps—

In a case where a substrate is used as the metal layer, the method of manufacturing the metal material for a medical device of the present disclosure may include a step of etching the substrate as another step. By etching, adhesion to the DLC layer can be further enhanced.

As a method of etching, a dry etching method such as an ion beam etching method or a plasma etching method can be used.

Examples of the gas used for etching include a rare gas (examples: helium (He), neon (Ne), argon (Ar), krypton (Kr), and xenon (Xe)), a halogen-based gas containing a halogen atom (examples: $CCl_4$, $CClF_3$, $AlF_3$, and $AlCl_3$), $O_2$, $N_2$, CO, and $CO_2$.

The gas may be used alone, or may be a mixed gas of two or more.

The etching step is preferably a step of plasma-etching the surface of the substrate.

The method of manufacturing the metal material for a medical device of the present disclosure may include a step of further forming a coating layer containing a medical agent on the DLC layer as another step.

A medical agent release layer (for example, a polymer layer including a medical agent and a polymer) containing a target medical agent can be provided on at least a part of the DLC layer. This makes it possible to impart a medical agent release function while having excellent followability and flexibility as described above.

The medical agent may be selected according to a purpose such as killing a target cell.

<Medical Device>

The medical device of the present disclosure includes the aforementioned metal material for a medical device of the present disclosure.

Examples of the medical device of the present disclosure include a stent, a catheter device, an endoscope device, a fixing device such as a bolt or a screw, an artificial heart, an artificial hip joint, and a fixing plate. The medical device of the present disclosure is suitable as a stent, is suitable as a stent used for a systemic blood vessel of a human body, and is more suitable as a stent used for a lower limb blood vessel, a cerebral blood vessel, a pulmonary blood vessel, a cardiovascular blood vessel, or a trunk blood vessel.

The lower limb refers to the entire leg, and refers to from the hip joint to the fingertip, and includes three major joints of the hip joint, the knee joint, and the ankle joint and a portion of the toe.

EXAMPLES

Hereinafter, the present invention will be described more specifically with reference to examples, but the present invention is not limited to the following examples unless it goes beyond the gist of the present invention.

Example 1

—1. Preparation of Substrate (Metal Layer)—

As substrates, a NiTi alloy substrate and a silicon (Si) substrate were prepared for chemical composition analysis and evaluation of adhesion. Furthermore, in order to evaluate blood compatibility, a NiTi alloy substrate was prepared. Moreover, in order to evaluate the followability using a substrate assuming a stent, a NiTi wire was prepared. A thickness of the substrates was 380 μm, and a diameter of the wire was 150 μm.

—2. Preparation of Raw Material Gas—

As a raw material for preparing a raw material gas, the following compounds were prepared.

Silane compound: tetramethylsilane ($Si(CH_3)_4$)

Fluorine-containing aliphatic hydrocarbon: octafluoropropane ($C_3F_8$)

—3. Formation of DLC Layer—

A DLC layer containing F and Si was film-formed on the substrate or the wire by the following procedure.

(1) Etching Treatment

First, in order to improve the adhesion of a surface of the substrate, the surface of each substrate was subjected to surface treatment by plasma etching under the following conditions.

<Etching Conditions>

Etching device: YH-100NX (manufactured by ONWARD GIKEN Co., Ltd.)

Etching gas: Argon (Ar) gas

Etching time: 10 to 1000 seconds

Gas flow rate: 10 mL/min (2) Film Formation

An inductively coupled high frequency plasma chemical vapor deposition (ICP-CVD) device YH-100NX manufactured by ONWARD GIKEN Co., Ltd. was prepared, and each substrate was sequentially disposed within this chamber. Vaporized tetramethylsilane (TMS; silane compound) and octafluoropropane (OFP/aka: propane octafluoride; fluorine-containing aliphatic hydrocarbon) were introduced to form a film on the surface of each substrate.

The film formation was performed by controlling a partial pressure PSi of TMS and a partial pressure PF of OFP introduced into the chamber. Specifically, as shown in Table 1, TMS was first introduced at a flow rate of 6 sccm (PSi: 0.22 Pa), and OFP was introduced by gradually increasing a flow rate to 50 sccm (PF: 0.53 Pa) while maintaining the flow rate of TMS.

As described above, a medical material (metal material for a medical device) in which a 200 nm-thick DLC layer was formed on the substrate or the wire was prepared. The elemental composition of carbon, fluorine, and silicon in the DLC layer was measured by the following method.

—4. Measurement and Evaluation—

The following measurement and evaluation were performed on the DLC layer formed on the substrate or the wire.

(1. F Concentration and Si Concentration)

The F concentration and the Si concentration were determined by performing chemical composition analysis by the following method using a test sample in which the DLC layer was formed on the Si substrate or the NiTi alloy substrate. The measurement results are shown in Tables 2 and 3.

Using an XPS device (JPS-9010TR manufactured by JEOL Ltd.), the element contents (contents of C, F, Si and O) were determined from the spectrum measured on the outermost surface of the DLC layer and the surface of the DLC layer in contact with the substrate, and in the thickness direction of the DLC layer. Note that the outermost surface of the DLC layer is the surface of the DLC layer at an opposite side from a side in contact with the substrate.

Specific operations are as follows.

a) MgKα was used as an X-ray source, and analysis of C, F, Si, and O at each surface of an untreated DLC layer formed on each substrate was performed under X-ray generation conditions of 10 kV and 10 mA.

b) Next, each surface of the DLC layer was etched for 10 seconds using an Ar gas cluster ion beam.

c) C, F, Si, and O in the inside of the DLC layer etched in the above b) were analyzed in the same manner as in the above a).

d) The element contents at the surface and in the inside of the DLC layer were determined from the spectra acquired by the respective measurements. The element contents were calculated by a correlation sensitivity coefficient method from the spectrum area of each element acquired by the measurement.

Note that the element contents at the surface of the DLC layer in contact with the substrate and the element contents in the thickness direction of the DLC layer were determined by measuring the inside of the layer by etching the DLC layer. The element contents in the thickness direction of the DLC layer were determined by etching the DLC layer at predetermined intervals in the thickness direction, measuring the element distribution in the thickness direction inside the layer and in a plane direction parallel to the outermost surface, and performing integral calculation of the amounts of carbon, fluorine, and silicon from the outermost surface toward the thickness direction in the DLC layer.

Furthermore, in the measurement of the element distribution at the outermost surface of the DLC layer and in the thickness direction of the DLC layer, a DLC layer formed using the silicon (Si) substrate as the substrate was used. In the measurement at the surface of the DLC layer in contact with the substrate, a DLC layer formed using the NiTi alloy substrate as the substrate was used.

(2. Adhesion)

Adhesion of the DLC layer to the NiTi alloy substrate was evaluated by a scratch test. Specifically, a peeling critical load of the DLC layer was obtained 5 times according to the following procedure using a nano-scratch tester (CSR5000 manufactured by RHESCA CORPORATION), and an average value of the 5 times was calculated to be an index for evaluating the adhesion. The evaluation results are shown in Table 4 and FIG. 9.

<Procedure>

(1) Using a diamond indenter having a tip diameter φ of 5 μm, the surface of the DLC layer formed on the NiTi alloy substrate was scanned under the following conditions.

<Test Conditions>

Maximum load: 100 mN

Load application speed: 1.67 mN/s

Scratch length: 600 μm

Number of tests: 5 times (2) A peeling start point of the DLC layer generated at the time of scanning was measured, and a peeling critical load was calculated.

(3) Based on the results of the peeling critical load, evaluation was performed according to the following evaluation criteria.

<Evaluation Criteria>

A: Extremely excellent adhesion was exhibited.

B: Adhesion was exhibited to such an extent that practical use was not hindered.

C: Poor in adhesion.

(3. Followability)

The followability of the DLC layer to deformation of the NiTi wire was evaluated by electron microscope observation. Specifically, a sample having a DLC layer formed on the NiTi wire that is most easily deformed was used as a test sample, and this test sample was bent at a bending angle of 120°. Then, the test sample in a bent state was observed with a scanning electron microscope (SEM), and the followability of the DLC layer in a state deformed by bending was evaluated according to the following evaluation criteria. The evaluation results are shown in Table 4.

<Evaluation Criteria>

A: High flexibility and extremely excellent followability were exhibited.

B: Flexibility was slightly insufficient, and peeling of the DLC layer was not observed, but cracks were observed in the DLC layer.

C: Poor flexibility, and a peeling portion was observed in the DLC layer.

(4. Blood Compatibility)

Platelets were adhered to a NiTi alloy substrate or a substrate with a DLC layer in which the DLC layer is formed on a NiTi alloy substrate prepared as samples, and a platelet adherence test for evaluating antithrombogenicity of the sample was performed to evaluate blood compatibility. Since a main cause of thrombus formation on a biological material in a blood vessel is blood coagulation caused by a material surface characteristic called an intrinsic blood coagulation factor, it can be said that blood compatibility is higher as the adherence amount of platelets is smaller.

The test was performed according to the following procedure using the NiTi alloy substrate and the substrate with the DLC layer. The results are shown in Table 4.

<Procedure>

(1) Platelet rich plasma (PRP) separated from the blood of a healthy adult was dropped and applied in an amount of 1 mL onto each of the NiTi alloy substrate and the substrate with the DLC layer in which the DLC layer was formed on the NiTi alloy substrate, and incubated under the conditions of 37° C. and a $CO_2$ partial pressure ratio of 5% in an atmosphere for 60 minutes using a $CO_2$ incubator.

The platelet rich plasma (PRP) is a solution of platelet-rich blood separated from the blood.

(2) After incubation, blood on the NiTi alloy substrate or the sample was carefully sucked and washed with saline.

(3) After dehydration and fixation of platelets adhered to the surface of the NiTi alloy substrate or the surface of the DLC layer of the substrate with the DLC layer, platelets adhered to the surface of the NiTi alloy substrate or the surface of the DLC layer of the substrate with the DLC layer were observed using a differential interference microscope which is a kind of optical microscope.

(4) The adherence state of platelets observed in the micrograph was evaluated according to the following evaluation criteria.

Evaluation Criteria

A: Adherence of platelets is extremely small.

B: Adherence of platelets is observed.

C: Adherence of platelets is remarkably observed.

Example 2

A DLC layer was formed in the same manner as in Example 1 except that the film formation was performed by controlling the partial pressure $P^{Si}$ of TMS and the partial pressure $P^{F}$ of OFP introduced into the chamber such that the content ratio of fluorine and silicon changed in the thickness direction of the DLC layer as shown in Table 1, and the measurement and evaluation were further performed. Specifically, the film formation was performed by first introducing TMS at a flow rate of 6 sccm ($P^{Si}$:0.22 Pa), and gradually increasing OFP to a flow rate of 50 sccm ($P^F$:0.53 Pa) while gradually decreasing the flow rate of TMS. The measurement and evaluation results are shown in Tables 2 and 3, and FIG. 9.

Example 3

A DLC layer was formed in the same manner as in Example 1 except that the film formation was performed by controlling the partial pressure $P^{Si}$ of TMS, the partial pressure $P^F$ of OFP, and the partial pressure $P^C$ of acetylene introduced into the chamber such that the content ratio of carbon, fluorine, and silicon changed in the thickness direction of the DLC layer as shown in Table 1, and the measurement and evaluation were further performed.

Specifically, the film formation was performed by first introducing TMS at a flow rate of 6 sccm ($P^{Si}$:0.22 Pa), and gradually increasing OFP to a flow rate of 50 sccm ($P^F$:0.53 Pa) and gradually increasing acetylene to a flow rate of 3 sccm ($P^F$:0.11 Pa) while gradually decreasing the flow rate of TMS.

Figure 2:
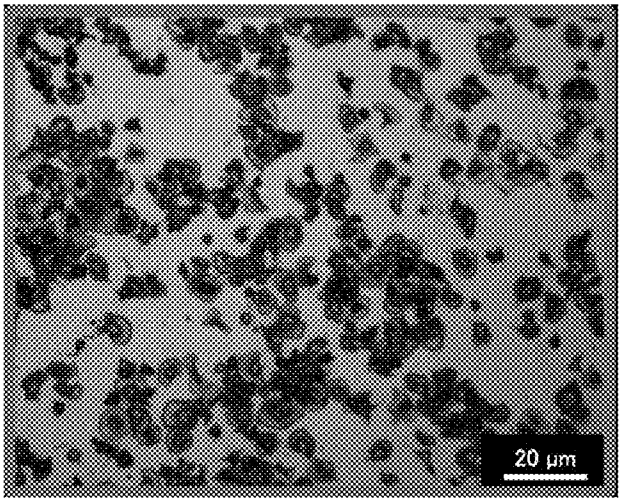
FIG. 2 is an SEM photograph illustrating an adherence state of platelets on a NiTi alloy substrate in which a DLC layer is not formed.
Figure 3:
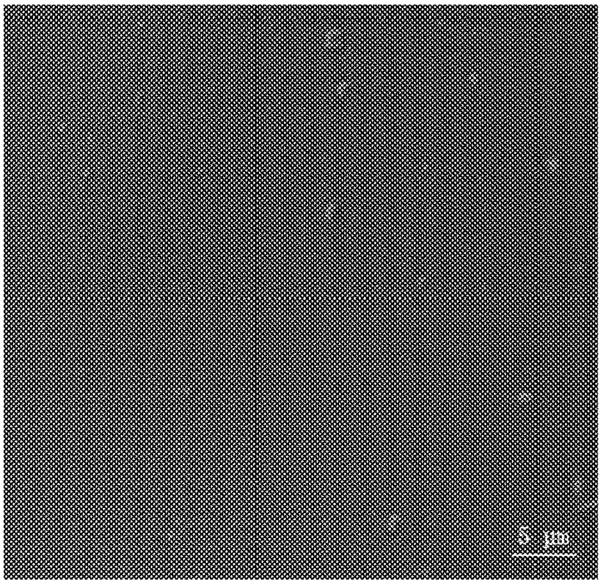
FIG. 3 is an SEM photograph illustrating a peeled state (followability) in the test sample of Example 3 in which a single layer-DLC layer is formed on a NiTi alloy wire.
Figure 9:
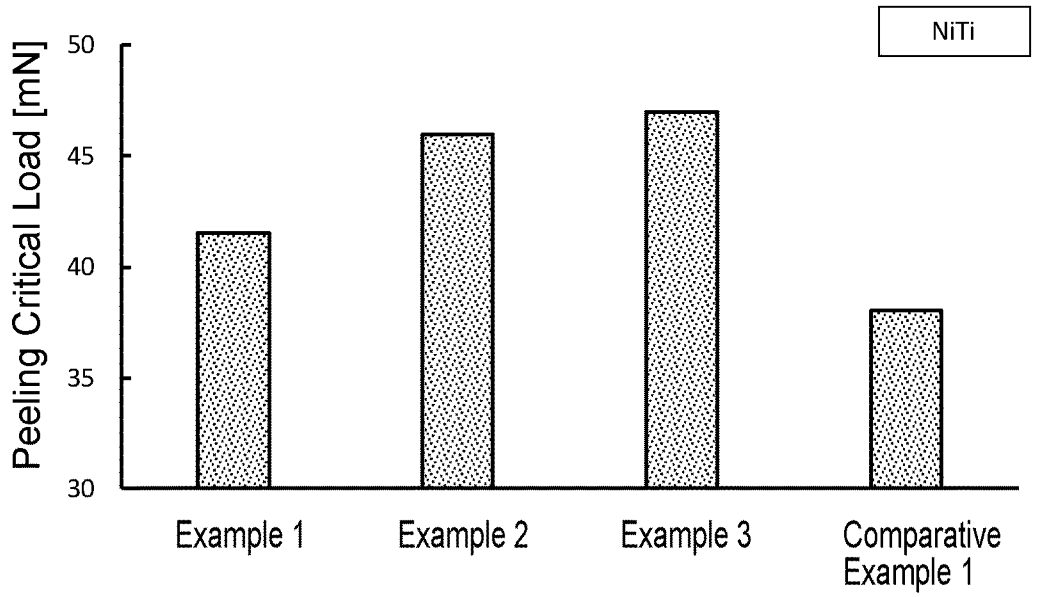
FIG. 9 is a graph illustrating adhesion (to the NiTi alloy substrate) of the DLC layers in Examples 1 to 3 and Comparative Example 1 in comparison.

The measurement and evaluation results are shown in Tables 2 and 3, FIG. 1 (FIG. 2 as comparison), FIG. 3, and FIG. 9. In FIG. 9, a white portion seen in the observation field of view is a region where peeling occurs.

Example 4

A DLC layer was formed in the same manner as in Example 1 except that the type of the substrate was changed from the NiTi alloy to a CoCr alloy in Example 1, and the measurement and evaluation were further performed. The measurement and evaluation results are shown in Table 4.

Examples 5 to 7

Figure 4:
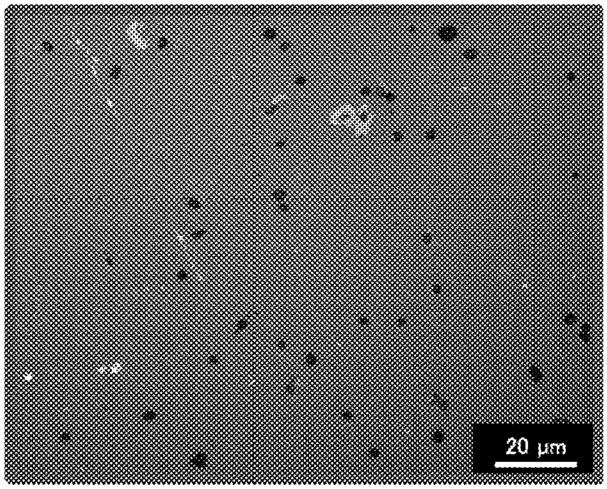
FIG. 4 is an SEM photograph illustrating an adherence state of platelets in a test sample of Example 7 in which a single layer-DLC layer is formed on a SUS316L (stainless steel) substrate.
Figure 5:
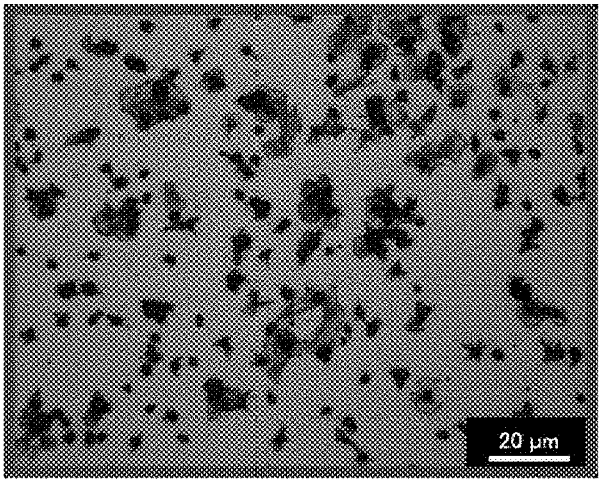
FIG. 5 is an SEM photograph illustrating an adherence state of platelets on a stainless steel substrate in which a DLC layer is not formed.

A DLC layer was formed in the same manner as in Example 1 except that the type of the substrate was changed from the NiTi alloy to SUS316L (stainless steel) in each of Examples 1 to 3, and the measurement and evaluation were further performed. The measurement and evaluation results are shown in Table 4, FIG. 4 (FIG. 5 as a comparison), and FIG. 10.

Comparative Example 1

As a substrate, a NiTi alloy substrate was prepared in the same manner as in Example 1. After an argon bombardment treatment was performed on the surface of the substrate for about 10 minutes, a SiC layer having a thickness of about 100 nm was formed using tetramethylsilane (TMS) as a raw material gas. Next, using tetramethylsilane (TMS) and acetylene ($C_2H_2$) as raw material gases, a Si-DLC layer having a thickness of about 100 nm was formed as a first DLC layer on a surface of the SiC layer. Thereafter, by using perfluoropropane ($C_3F_8$) and acetylene ($C_2H_2$) as raw material gases, a fluorine-containing DLC layer (F-DLC layer) having a thickness of about 200 nm was formed as a second DLC layer on a surface of the Si-DLC layer. Note that in the formation of the SiC layer, the Si-DLC layer, and the F-DLC layer, each gas flow rate, reaction time, and the like were appropriately adjusted so as to obtain each layer having the aforementioned thickness.

Figure 8:
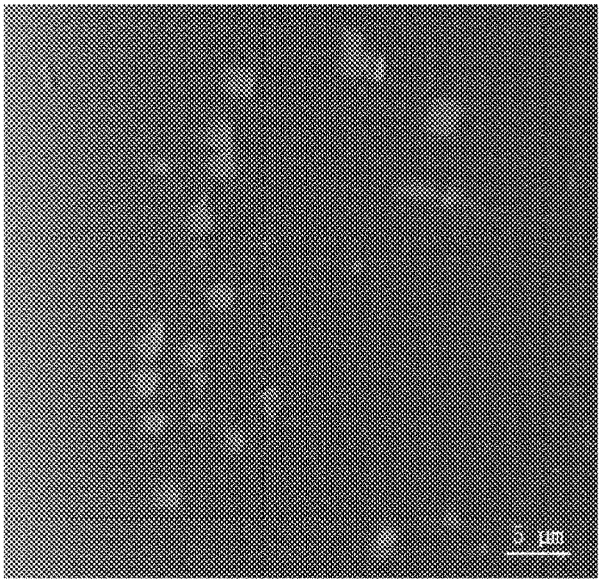
FIG. 8 is an SEM photograph illustrating a peeled state (followability) in the test sample of Comparative Example 1 in which a DLC layer having a multilayer structure is formed on a NiTi alloy wire.
Figure 13:
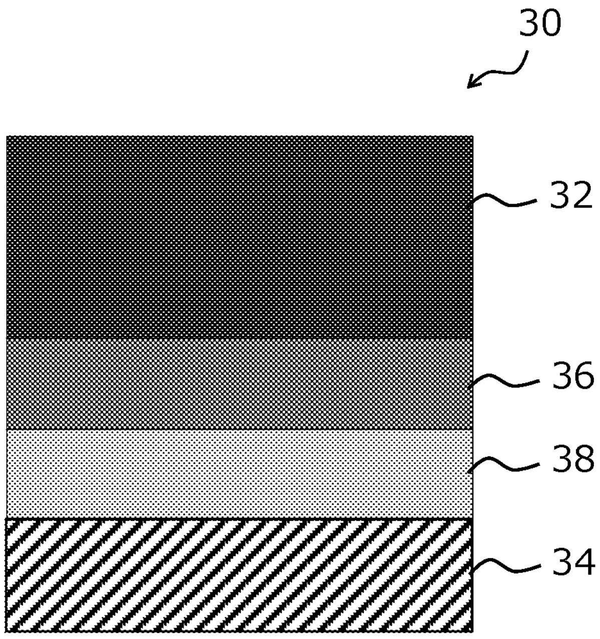
FIG. 13 is a schematic cross-sectional view illustrating a conventional metal material for a medical device.

As described above, as shown in FIG. 13, a stent having a layered structure of the F-DLC layer, the Si-DLC layer, the SiC layer, and the substrate was produced. The produced stent was measured and evaluated in the same manner as in Example 1. The measurement and evaluation results are shown in Tables 3 and 4, FIG. 6, FIG. 8, and FIG. 9. In FIG. 8, a white portion seen in the observation field of view is a region where peeling occurs.

Comparative Example 2

Figure 7:
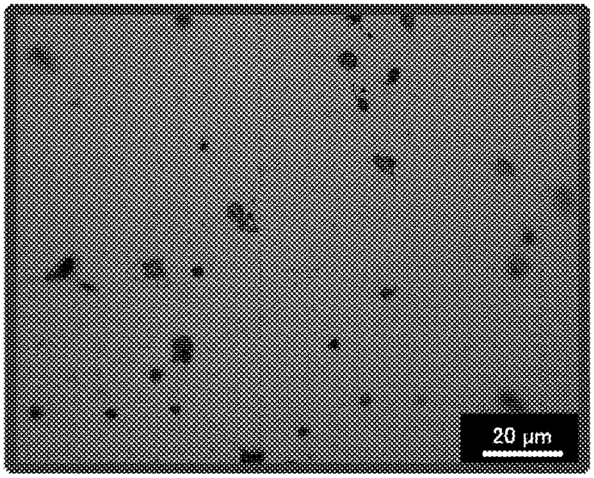
FIG. 7 is an SEM photograph illustrating an adherence state of platelets in a test sample of Comparative Example 2 in which a DLC layer having a multilayer structure is formed on a SUS316L (stainless steel) substrate.
Figure 10:
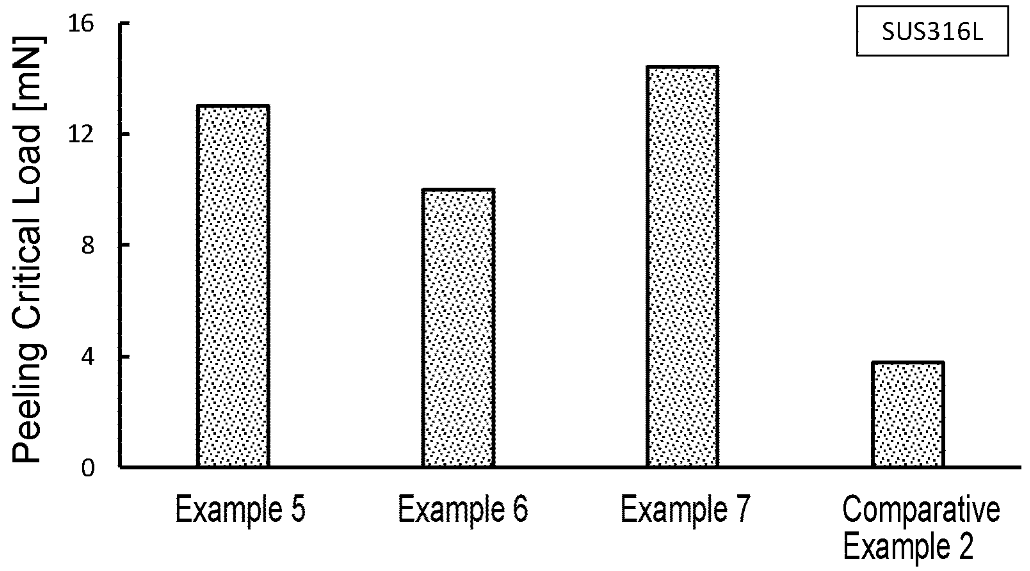
FIG. 10 is a graph illustrating adhesion (to the stainless steel substrate) of the DLC layers in Examples 5 to 7 and Comparative Example 2 in comparison.

Measurement and evaluation were performed in the same manner as in Comparative Example 1 except that the type of the substrate was changed from the NiTi alloy to SUS316L (stainless steel) in Comparative Example 1. The measurement results are shown in FIGS. 7 and 10.

TABLE 1

| | | Example 1 Start Point | → End Point | Example 2 Start Point | → End Point | Example 3 Start Point | → End Point |
|---|---|---|---|---|---|---|---|
| TMS | Flow Rate [sccm] | 6 | 6 | 6 | 1 | 6 | 0 |
| | Pressure [Pa] | 0.22 | 0.22 | 0.22 | 0.05 | 0.22 | 0 |
| $C_3F_8$ | Flow Rate [sccm] | 0 | 50 | 0 | 50 | 0 | 50 |
| | Pressure [Pa] | 0 | 0.53 | 0 | 0.53 | 0 | 0.53 |
| $C_2F_2$ | Flow Rate [sccm] | 0 | 0 | 0 | 0 | 0 | 3 |
| | Pressure [Pa] | 0 | 0 | 0 | 0 | 0 | 0.11 |

TABLE 2

| | F Concentration in DLC Layer | | | | Si Concentration in DLC Layer | | | | |
|---|---|---|---|---|---|---|---|---|---|
| | Cf | Increase/Decrease of Concentration in Thickness Direction | Outermost Surface of DLC Layer [at %] | Surface of DLC Layer in Contact with Substrate [at %] | Cs | Increase/Decrease of Concentration in Thickness Direction | Outermost Surface of DLC Layer [at %] | Surface of DLC Layer in Contact with Substrate [at %] | $D^F$:$D^S$ |
| Example 1 | 32.2 | Gradually Increase from Substrate Side | 16.1 | 0.5 | 0.364 | Gradually Decrease from Substrate Side | 14.6 | 40.1 | 1.1:1 |

TABLE 2-continued

| | F Concentration in DLC Layer | | | | Si Concentration in DLC Layer | | | | |
|---|---|---|---|---|---|---|---|---|---|
| | Cf | Increase/Decrease of Concentration in Thickness Direction | Outermost Surface of DLC Layer [at %] | Surface of DLC Layer in Contact with Substrate [at %] | Cs | Increase/Decrease of Concentration in Thickness Direction | Outermost Surface of DLC Layer [at %] | Surface of DLC Layer in Contact with Substrate [at %] | $D^F:D^S$ |
| Example 2 | 68.4 | Gradually Increase from Substrate Side | 34.2 | 0.5 | 0.034 | Gradually Decrease from Substrate Side | 1.4 | 41.0 | 24.4:1 |
| Example 3 | 154.8 | Gradually Increase from Center of Thin Film to Surface Side | 61.9 | 0.4 | 0.017 | Gradually Decrease from Center of Thin Film to Surface Side | 0.7 | 41.5 | 88.4:1 |
| Comparative Example 1 | 87.2 | Multilayer | 52.3 | 0.6 | 0.027 | Multilayer | 1.1 | 41.1 | 47.5:1 |

TABLE 3

| | Content Concentration in DLC Layer [at %] (Integral Calculated Value) | | | Ratio of Thickness from Outermost Surface of DLC Layer to Position Where F Concentration is below 10 at % of Total Content of C, F and Si with respect to Layer Thickness (Ratio of Depth from Outermost Surface in Thickness |
|---|---|---|---|---|
| | C | F | Si | Direction with respect to Thickness of DLC Layer) |
| Example 1 | 72% | 12% | 17% | 20% |
| Example 2 | 69.0% | 7.3% | 23.7% | 6% |
| Example 3 | 68.1% | 8.0% | 23.9% | 7% |
| Comparative Example 1 | 71.6% | 11.7% | 16.7% | 34% |

TABLE 4

| | | | Evaluation | | |
|---|---|---|---|---|---|
| | Type of Substrate | DLC Layer | Adhesion | Followability | Blood Compatibility |
| Example 1 | NiTi Alloy | Single Layer | B | A | A |
| Example 3 | NiTi Alloy | Single Layer | A | A | A |
| Example 4 | CoCr Alloy | Single Layer | A | A | A |
| Example 5 | SUS316L | Single Layer | A | A | A |
| Example 7 | SUS316L | Single Layer | A | A | A |
| Comparative Example 1 | NiTi Alloy | Two Layers Layered | C | B | B |

As shown in Table 4, in each of Examples in which the fluorine (F) concentration and the silicon (Si) concentration in the single layer-DLC layer were gradually changed in the thickness direction, good results were obtained in adhesion, followability, and blood compatibility as compared with Comparative Example 1 having a multilayer structure including F and Si in separate layers.

Figure 6:
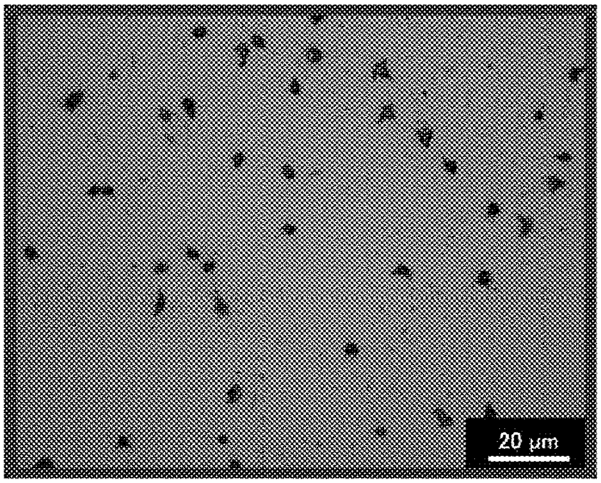
FIG. 6 is an SEM photograph illustrating an adherence state of platelets in a test sample of Comparative Example 1 in which a DLC layer having a multilayer structure is formed on a NiTi alloy substrate.

As is clear from comparison between FIG. 1 (Example 3) and FIG. 6 (Comparative Example 1), it was confirmed that in the test sample (metal material for a medical device) of Example 3 having the single layer-DLC layer on the NiTi alloy substrate, the number of adhering platelets was significantly reduced as compared with Comparative Example 1 in which the DLC layer had a multilayer layered structure. Note that in the NiTi alloy substrate having no DLC layer as a Reference Example, it is clear that the degree of adherence of platelets is remarkable as shown in FIG. 2. As is clear from comparison between FIG. 4 (Example 7) and FIG. 7 (Comparative Example 2), similar results were obtained between Example 7 and Comparative Example 2 in which the NiTi alloy substrate was replaced with the SUS316L (stainless steel) substrate. Furthermore, this is also clear from comparison between FIG. 4 (Example 7) and FIG. 5 (Reference Example without DLC layer). That is, as in the case of using the NiTi alloy substrate, it can be seen that in the case of having the single layer-DLC layer on the stainless steel substrate (the test sample (metal material for a medical device) of Example 7), the number of adhering platelets is significantly reduced as compared with the case of using the stainless steel substrate having no DLC layer.

Furthermore, as is clear from comparison between FIG. 3 (Example 3) and FIG. 8 (Comparative Example 1), in the stent using the NiTi alloy wire, it was confirmed that in the test sample of Example 3 (metal material for a medical device) having the single layer-DLC layer on the NiTi alloy wire, peeling of the DLC layer was suppressed and the followability was excellent as compared with Comparative Example 1 in which the DLC layer had a multilayer layered structure.

With respect to the adhesion of the DLC layer, as shown in Table 4 and FIGS. 9 and 10, Examples 1 to 3 and Examples 5 to 7 in which the fluorine (F) concentration and the silicon (Si) concentration in the single layer-DLC layer were gradually changed in the thickness direction were excellent as compared with Comparative Example 1 or Comparative Example 2 each having a multilayer structure including F and Si in separate layers.

The invention claimed is:

1. A metal material for a medical device, the metal material comprising:

a metal layer; and a diamond-like carbon layer provided on the metal layer and containing fluorine and silicon in a single layer, wherein:

in the diamond-like carbon layer, a concentration of the fluorine at a surface at an opposite side from a side facing the metal layer is larger than a concentration of the fluorine at a surface at the side facing the metal layer, in a thickness direction of the diamond-like carbon layer, in the diamond-like carbon layer, a concentration of the silicon at a surface at an opposite side from a side facing the metal layer is smaller than a concentration of the silicon at a surface at the side facing the metal layer, in a thickness direction of the diamond-like carbon layer, and a ratio (DF:DS) of a concentration DF of the fluorine with respect to a concentration DS of the silicon at a surface of the diamond-like carbon layer at an opposite side from a side facing the metal layer is greater than 1:1 and less than or equal to 90:1, and a composition at the surface of the diamond-like carbon layer at the opposite side contains a greater amount of fluorine than silicon.

2. The metal material for a medical device according to claim 1, wherein a total concentration of the fluorine contained in the diamond-like carbon layer is from 7 atom % to 10 atom % with respect to a total concentration of carbon, fluorine, and silicon.

3. The metal material for a medical device according to claim 1, wherein a total concentration of the silicon contained in the diamond-like carbon layer is from 17 atom % to 25 atom % with respect to a total concentration of carbon, fluorine, and silicon.

4. The metal material for a medical device according to claim 1, wherein, in the diamond-like carbon layer, a ratio Cf of the concentration of the fluorine at the surface at the opposite side from the side facing the metal layer with respect to the concentration of the fluorine at the surface at the side facing the metal layer satisfies a relationship $1<Cf\leq155$.

5. The metal material for a medical device according to claim 1, wherein a concentration of the fluorine contained in the diamond-like carbon layer gradually increases from the side facing the metal layer toward the opposite side from the side facing the metal layer in the thickness direction of the diamond-like carbon layer.

6. The metal material for a medical device according to claim 1, wherein, in the diamond-like carbon layer, a ratio Cs of the concentration of the silicon at the surface at the opposite side from the side facing the metal layer with respect to the concentration of the silicon at the surface at the side facing the metal layer satisfies a relationship $0.015\leq Cs<1$.

7. The metal material for a medical device according to claim 1, wherein the concentration of the silicon contained in the diamond-like carbon layer gradually decreases from the side facing the metal layer toward the opposite side from the side facing the metal layer in the thickness direction of the diamond-like carbon layer.

8. The metal material for a medical device according to claim 1, wherein the diamond-like carbon layer is provided as an outermost layer on the metal layer.

9. The metal material for a medical device according to claim 1, wherein the metal layer contains at least one metal selected from the group consisting of titanium, nickel, cobalt, chromium, tantalum, platinum, gold, alloys thereof, and stainless steel.

10. The metal material for a medical device according to claim 9, wherein the metal layer contains a nickel-titanium alloy, a cobalt-chromium alloy, or stainless steel.

11. The metal material for a medical device according to claim 1, wherein the metal material is used in a stent.

12. The metal material for a medical device according to claim 11, wherein the stent is a stent for a systemic blood vessel.

13. The metal material for a medical device according to claim 1, wherein the diamond-like carbon layer has an atomic percentage concentration of fluorine at an outermost surface of 16.1 at % or more and 61.9 at % or less, and an atomic percentage concentration of silicon at an outermost surface of 0.7 at % or more and 14.6 at % or less.

14. A medical device, comprising the metal material for a medical device according to claim 1.

15. The medical device according to claim 14, wherein the medical device is a stent.

16. The medical device according to claim 15, wherein the stent is a stent for a lower limb blood vessel.

17. A method of manufacturing a metal material for a medical device according to claim 1, the method comprising forming a diamond-like carbon layer containing fluorine and silicon on a metal layer by vapor deposition, by a vapor phase growth method using a mixed raw material obtained by mixing a silane compound and a fluorine-containing aliphatic hydrocarbon as raw materials.

* * * * *